US012806369B2

(12) United States Patent
Davis et al.

(10) Patent No.: US 12,806,369 B2
(45) Date of Patent: Nov. 24, 2026

(54) PRE-CURVED CATHETER

(71) Applicant: Bard Access Systems, Inc., Salt Lake City, UT (US)

(72) Inventors: Zachary S. Davis, Sandy, UT (US); Daniel B. Blanchard, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 17/374,812

(22) Filed: Jul. 13, 2021

(65) Prior Publication Data

US 2022/0016388 A1 Jan. 20, 2022

Related U.S. Application Data

(60) Provisional application No. 63/051,755, filed on Jul. 14, 2020.

(51) Int. Cl.
*A61M 25/00* (2006.01)
*A61M 25/06* (2006.01)

(52) U.S. Cl.
CPC ........ *A61M 25/0041* (2013.01); *A61M 25/06* (2013.01); *A61M 2205/0216* (2013.01)

(58) Field of Classification Search
CPC ...... A61M 25/0041; A61M 2025/0095; A61M 25/0606; A61M 25/0102; A61B 17/34
See application file for complete search history.

(56) References Cited

U.S. PATENT DOCUMENTS 3,539,034 A 11/1970 Tafeen
3,782,381 A 1/1974 Winnie
4,738,667 A 4/1988 Galloway
4,747,840 A 5/1988 Adika et al.
5,207,647 A 5/1993 Phelps
5,345,937 A 9/1994 Middleman et al.
(Continued)

FOREIGN PATENT DOCUMENTS

EP 3530309 A1 * 8/2019 ........ A61M 25/0041
WO 16172281 A1 10/2016
(Continued)

OTHER PUBLICATIONS

"Central Angle, CueMath, https://www.cuemath.com/geometry/central-angle/" (Year: NA).*
(Continued)

*Primary Examiner* — Courtney Fredrickson
*Assistant Examiner* — Kayla M. Turkowski
(74) *Attorney, Agent, or Firm* — Rutan & Tucker LLP

(57) ABSTRACT

A pre-curved catheter includes a hub and an elastically deformable tubular body coupled to the hub. The elastically deformable tubular body can include a first body segment including a first body segment length including a lumen, a second body segment distal the first body segment, the second body segment including a second body segment length, and a first transitional body segment interposed between the first body segment and the second body segment. The first transitional body segment can include a selected first degree of curvature representing an angular change between a direction in an orientation of the first body segment and a direction in an orientation of the second body segment.

7 Claims, 8 Drawing Sheets

(56) References Cited

U.S. PATENT DOCUMENTS

| | | | | |
|---|---|---|---|---|
| 5,423,770 | A | 6/1995 | Yoon | |
| 5,693,030 | A | 12/1997 | Lee et al. | |
| 5,807,339 | A | 9/1998 | Bostrom et al. | |
| 5,876,385 | A * | 3/1999 | Ikari | A61M 25/0041 604/523 |
| 5,885,247 | A | 3/1999 | Slagboom | |
| 6,086,548 | A | 7/2000 | Chaisson et al. | |
| 6,592,559 | B1 | 7/2003 | Pakter et al. | |
| 6,607,511 | B2 | 8/2003 | Halseth et al. | |
| 6,656,166 | B2 | 12/2003 | Lurie et al. | |
| 7,713,215 | B2 | 5/2010 | Shriver | |
| 8,252,004 | B2 | 8/2012 | Rosenberg et al. | |
| 8,562,573 | B1 | 10/2013 | Fischell | |
| 8,628,551 | B2 | 1/2014 | Hanson et al. | |
| 9,011,380 | B2 | 4/2015 | Tkebuchava | |
| 9,314,593 | B2 | 4/2016 | Schaeffer | |
| 9,408,667 | B2 | 8/2016 | Okazaki et al. | |
| 10,307,567 | B2 | 6/2019 | Carnevale | |
| 10,463,781 | B2 | 11/2019 | Vidovich | |
| 2005/0209610 | A1 | 9/2005 | Carrison | |
| 2009/0105724 | A1 * | 4/2009 | Yoshizaki | A61M 31/00 606/129 |
| 2010/0030191 | A1 * | 2/2010 | McFerran | A61M 25/0045 604/523 |
| 2013/0158396 | A1 | 6/2013 | Vidovich | |
| 2013/0237958 | A1 | 9/2013 | Arrigo | |
| 2013/0317410 | A1 | 11/2013 | Dextradeur | |
| 2015/0289753 | A1 | 10/2015 | Kimura | |
| 2021/0290913 | A1 * | 9/2021 | Horst | A61M 25/09 |

FOREIGN PATENT DOCUMENTS

| | | | | |
|---|---|---|---|---|
| WO | 16191062 | A2 | 12/2016 | |
| WO | WO-2020210488 | A1 * | 10/2020 | A61M 25/0113 |

OTHER PUBLICATIONS

"Degree of Curvature, Integrated Publishing, http://www.tpub.com/integ/11b.htm" (Year: NA).*

PCT/US2021/041478 filed Jul. 13, 2021 International Search Report and Written Opinion dated Dec. 14, 2021.

* cited by examiner

PROXIMAL
DISTAL 200
214
222
216

200
214
222
216

300
316
328
318
332
320

300
316
328
318
332
320
PROXIMAL
DISTAL

PRE-CURVED CATHETER

PRIORITY

This application claims the benefit of priority to U.S. Provisional Application No. 63/051,755, filed Jul. 14, 2020, which is incorporated by reference in its entirety into this application.

BACKGROUND

With over the needle catheter placement, a medical professional has to insert the needle and catheter combination at an initial angle. Once the needle is removed, the proximal end of the catheter is placed flush against the skin while the distal end of the catheter resides within the lumen of a blood vessel. This increases the angle of the catheter which can create tension on the catheter and can lead to kinking (e.g., undesired bending) of the catheter at some distance from the catheter hub. Kinking in the catheter reduces the flow rate through the catheter and can necessitate catheter replacement. It would be beneficial to retain the initial angle of the catheter once is it placed inside the lumen of the vessel. This would reduce kink rates and potentially increase "first stick" success rates. Disclosed herein are a pre-curved catheter and method of use that address the foregoing.

SUMMARY

Disclosed herein is a pre-curved catheter and catheter insertion kit. The disclosed embodiments of the pre-curved catheter provide several advantages over conventional catheters. Particularly, embodiments of the disclosure have a significant reduction in kink rate while facilitating an easy transition into the lumen of the blood vessel.

In some embodiments, a pre-curved catheter including a hub; and an elastically deformable tubular body coupled to the hub, the elastically deformable tubular body including a first body segment including a first body segment length including a lumen; a second body segment distal the first body segment, the second body segment including a second body segment length; and a first transitional body segment being interposed between the first body segment and the second body segment and having a selected first degree of curvature representing an angular change between a direction in an orientation of the first body segment and a direction in an orientation of the second body segment.

In some embodiments, the pre-curved catheter includes the first degree of curvature that is measured from a first reference point being the distal end of the first body segment and is a negative obtuse angle within the range of −125° to −176°.

In some embodiments, the pre-curved catheter includes the first degree of curvature that is a positive obtuse angle, as measured from the first reference point and is within the range of 125° to 176°.

In some embodiments, the pre-curved catheter includes the elastically deformable tubular body includes a third body segment having a third body segment length and being distal to the second body segment; and a second transitional body segment having a second transitional body segment length interposed between the second body segment and the third body segment, and wherein the second transitional body segment includes a selected second degree of curvature, which provides the angular change between a direction in the orientation of the second body segment and a direction in the orientation of the third segment as measured from a second reference point that is the distal end of the second body segment.

In some embodiments, the pre-curved catheter includes a second degree of curvature that is measured from a second reference point being the distal end of the second body segment and is a positive obtuse angle within the range of 125° to 176°.

In some embodiments, the pre-curved catheter includes the second degree of curvature that is a negative obtuse angle as measured from the second reference point and is within a range of −125° to −176°.

In some embodiments, the pre-curved catheter includes the elastically deformable tubular body being sized to support an introducer needle having a diameter in a range of fourteen (14) to twenty-six (26) gauge.

Additionally disclosed herein is a catheter insertion kit including a pre-curved catheter including a hub; and the elastically deformable tubular body coupled to the hub, the elastically deformable tubular body including: a first body segment including a first body segment length including a lumen; a second body segment distal the first body segment, the second body segment including a second body segment length; and a first transitional body segment having a first transitional body segment length being interposed between the first body segment and the second body segment providing a selected first degree of curvature with an angular change between a direction in an orientation of the first body segment and a direction in an orientation of the second body segment as measured from a first reference point being a distal end of the first body segment; and an introducer needle including a rigid body having a proximal end, a distal end ending in a point, and a diameter in a range of 14-26 gauge, wherein a lumen of the elastically deformable tubular body of the pre-curved catheter is sized to receive the introducer needle for insertion and advancement through the lumen so that at least a portion of the rigid body extends past a distal end of the second body segment.

In some embodiments, the catheter insertion kit includes the first degree of curvature that is a negative obtuse angle as measured from the first reference point, within the range of −125° to −176°.

In some embodiments, the catheter insertion kit includes the first degree of curvature that is a positive obtuse angle as measured from the first reference point, within the range of 125° to 176°.

In some embodiments, the catheter insertion kit includes the elastically deformable tubular body includes a third body segment having a third body segment length and distal to the second body segment; and a second transitional body segment having a second transitional body segment length, interposed between the second body segment and the third body segment, and wherein the second transitional body segment includes a selected second degree of curvature, which provides the angular change between a direction in the orientation of the second body segment and a direction in the orientation of the third segment as measured from a second reference point that is the distal end of the second body segment.

In some embodiments, the catheter insertion kit includes the first degree of curvature that is a negative obtuse angle, as measured from the first reference point, and is within the range of −125° to −176° and the second degree of curvature that is a positive obtuse angle, as measured from the second reference point, and is within the range of 125° to 176°.

In some embodiments, the catheter insertion kit includes the first degree of curvature that is a positive obtuse angle, as measured from the first reference point, and is within the range of 125° to 176° and the second degree of curvature that is a negative obtuse angle, as measured from the second reference point, and is within the range of −125° to −176°.

Also disclosed herein is a method of inserting a pre-curved catheter, including obtaining a catheter insertion kit comprising: a pre-curved catheter comprising: a hub distally connected to an elastically deformable tubular body having a lumen configured to receive and support an introducer needle having a diameter in the range of 14 gauge to 26 gauge, the elastically deformable tubular body comprising a first body segment proximal the hub; a second body segment distal the first body segment; and a first transitional body segment being interposed between the first body segment and the second body segment, the first transitional body segment having a selected first degree of curvature which provides the angular change between a direction in the orientation of the first body segment and a direction in the orientation of the second body segment as measured from a first reference point that is a distal end of the first body segment being a negative obtuse angle; and an introducer needle comprising a rigid body having a proximal end, a distal end ending in a point, having a diameter in the range of 14 gauge to 26 gauge, and configured to be inserted into the lumen of the elastically deformable tubular body of the pre-curved catheter and extend through the lumen so that at least a portion of the rigid body extends past the distal end of the pre-curved catheter; inserting the introducer needle into lumen to provide a first force on first transitional body segment to change the first degree of curvature to approximately horizontal in the range of −179° to −181° as measured from the first reference point including that a portion of the rigid body extends past the distal end of the elongated deformable body; inserting the catheter insertion kit into a blood vessel lumen; and removing the first force on the first transitional body segment by removing the introducer needle from the lumen while the second body segment is within the blood vessel lumen wherein the first degree of curvature returns to a negative obtuse angle within the range of −125° to −176°.

In some embodiments, the method includes the first degree of curvature that is a positive obtuse angle as measured from the first reference point, and is within the range of 125° to 176°.

In some embodiments, the method includes the insertion of the introducer needle changing the first degree of curvature to be approximately horizontal in the range of 179° to 181° as measured from the first reference point.

In some embodiments, the method includes the catheter insertion kit which includes the elastically deformable tubular body of the pre-curved catheter including a third body segment distal the second body segment; and a second transitional body segment interposed between the second body segment and the third body segment; and the second transitional body segment having a selected second degree of curvature being a positive obtuse angle within the range of 125° to 176°, which provides the angular change between a direction in the orientation of the second body segment and a direction in the orientation of the third segment as measured from a second reference point that is the distal end of the second body segment.

In some embodiments, the method includes the inserting of the introducer needle into the lumen providing a first force on the first transitional body segment and the second transitional body segment to change the first degree of curvature to approximately horizontal in the range of −179° to 181° degrees as measured from the first reference point and the second degree of curvature to approximately horizontal in the range of 179° to 181° as measured form the second reference point.

In some embodiments, the method includes the removing the first force which includes the first degree of curvature returning to a negative obtuse angle within the range of −125° to −176° and the second degree of curvature returning to a positive obtuse angle within the range of 125° to 176°.

These and other features of the concepts provided herein will become more apparent to those of skill in the art in view of the accompanying drawings and following description, which describe particular embodiments of such concepts in greater detail.

DRAWINGS

Embodiments of the invention are illustrated by way of example and not by way of limitation in the figures of the accompanying drawings, in which like references indicate similar elements and in which.

DESCRIPTION

Figures 1A, 1B, 1C:
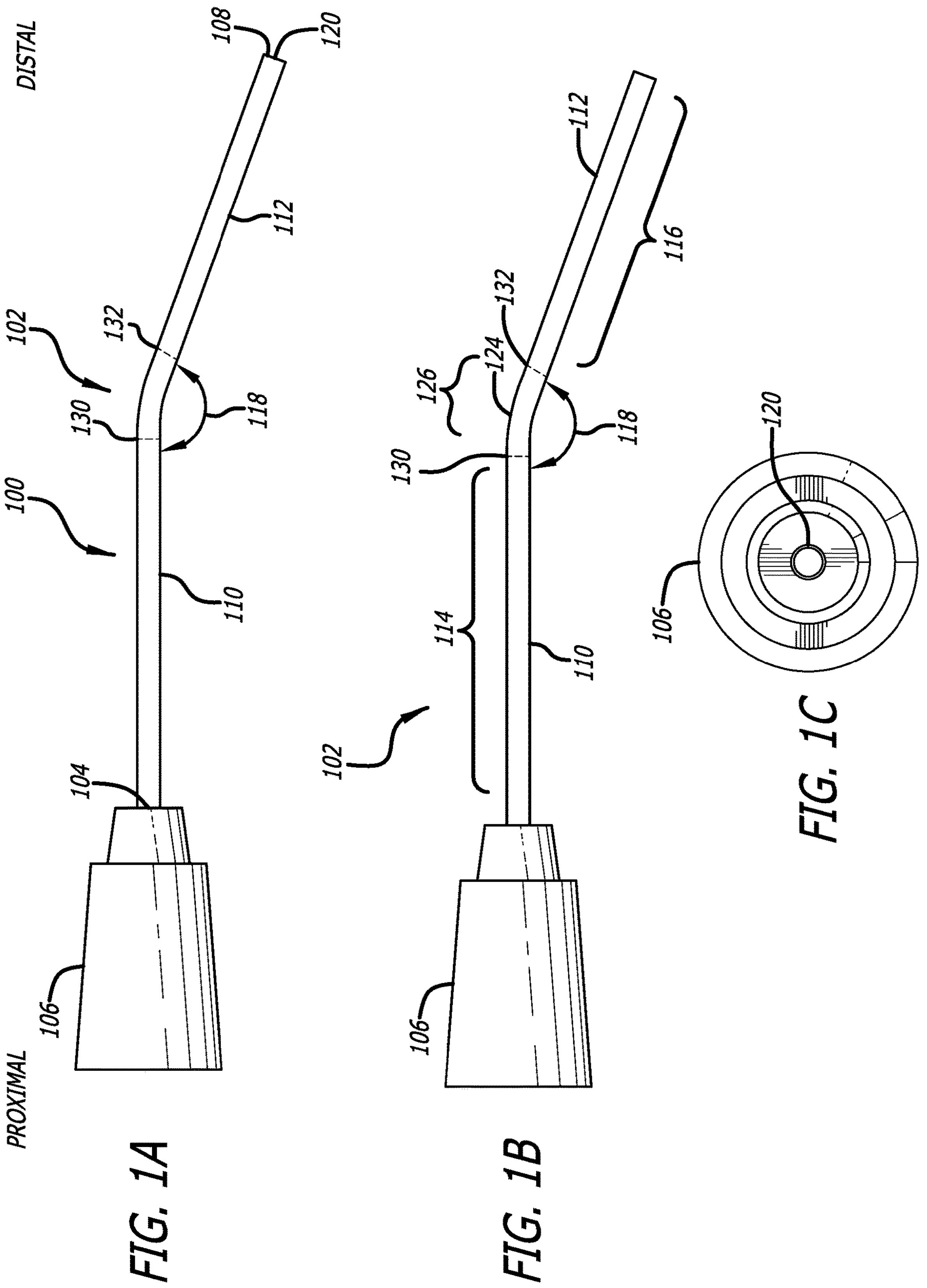
FIGS. 1A-1C illustrates a pre-curved catheter in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

The present disclosure generally relates to pre-curved catheters. FIG. 1A illustrates a pre-curved catheter 100 in accordance with some embodiments. The pre-curved catheter 100 includes a hub 106 distally connected to an elastically deformable tubular body 102 having a proximal opening 104, and a distal opening 108. In some embodiments as seen in FIG. 1B, the elastically deformable tubular body 102 can include a first body segment 110, a second body segment 112 and a transitional body segment 124 interposed between the first body segment 110 and the second body segment 112. In particular, according to an embodiment of the disclosure, the first body segment 110 is positioned proximal to the hub 106 and is deployed with a first length 114. The second body segment 112 is positioned distal to the first body segment 110 and is deployed with a second length 116. A lumen 120, as illustrated in FIG. 1C, is configured to receive and support an introducer needle having a diameter ranging from fourteen (14) gauge to twenty-six (26) gauge.

As further shown in FIG. 1B, the transitional body segment 124 may be configured with a transitional body segment length 126 and with a selected angular displacement between a first end 130 and a second end 132 of the transitional body segment 124. For example, the angular displacement between the first end 130 and the second end 132 of the transitional body segment 124 may be measured (and represented) by a first degree of curvature 118, which provides the angular change between a direction in the orientation of the first body segment 110 and a direction in the orientation of the second body segment 112.

As an illustrative embodiment, the first degree of curvature 118 can be measured from the first end 130 of the first transitional body segment 124, operating as a first reference point (e.g., a base angle such as interpreted as "zero" degrees) to the pre-curved catheter 100 at the second end 132 of the transitional body segment 124. It can be appreciated that the first reference point or base angle can have an insignificant deviation such as approximately 1° for example. It can also be appreciated that the degree of curvature 118 can be determined from any segment in the catheter and that the reference point can be formed in accordance with any segment in the pre-curved catheter 100. Furthermore, it can be appreciated that a segment is defined as a portion of a catheter of any size, such as within the range of 0.001-20 inches.

Figure 2A:
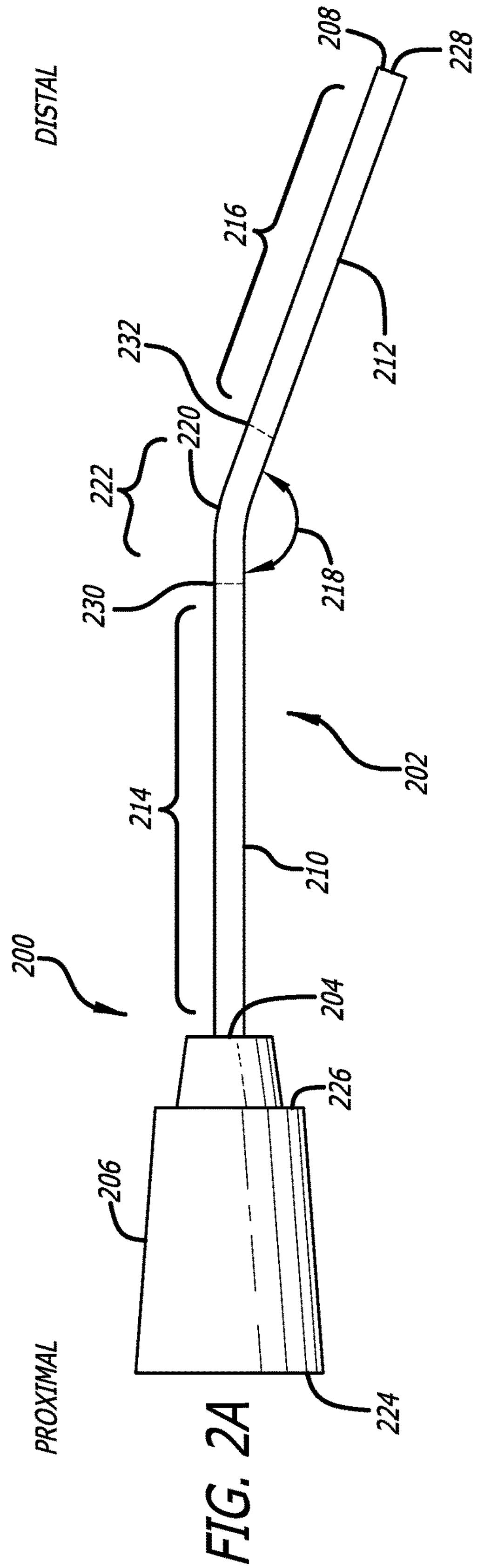
FIGS. 2A-2B illustrates different orientations of the pre-curved catheter in accordance with some embodiments illustrated in FIGS. 1A-1C.

FIG. 2A illustrates a more detailed relative embodiment of a pre-curved catheter 200 corresponding to the pre-curved catheter 100 illustrated in FIG. 1A-1B. In this example, the pre-curved catheter 200 further includes a molded hub 206 having a proximal end 224 and a distal end 226. The molded hub 206 is distally connected to an elastically deformable tubular body 202. The elastically deformable tubular body 202 includes a proximal opening 204, a distal opening 208 and a lumen 228 configured to receive and support an introducer needle having a diameter in the range of 14 gauge to 26 gauge. The elastically deformable tubular body 202 further includes a first body segment 210 having a first body segment length 214, a second body segment 212 having a second body segment length 216, and a first transition body segment 220 having a first transitional body length 222, interposed between the first body segment 210 and the second body segment 212. The first body segment 210 having a first body segment length 214 and the second body segment 212 having a second body segment length 216.

The first transitional body segment 220 may be configured with a selected angular displacement between a first end 230 and a second end 232 of the first transitional body segment 220. In some embodiments, the transitional body segment 220 can be downward sloping as illustrated in FIG. 2A. For example, the angular displacement between the first end 230 and the second end 232 of the first transitional body segment 220 may be measured (and represented) by a first degree of curvature 218, which provides the angular change between a direction in the orientation of the first body segment 210 and a direction in the orientation of the second body segment 212. The first degree of curvature 218 can be measured from a first reference point that can include the first end 230 of the first transitional body segment 220 (e.g., a bottom angular surface of the first end 230 to a corresponding bottom angular surface of the second end 232). In some embodiments, the first degree of curvature 218 can include a negative obtuse angle within the range of approximately −125° to −176° as measured from the first reference point.

Figure 2B:
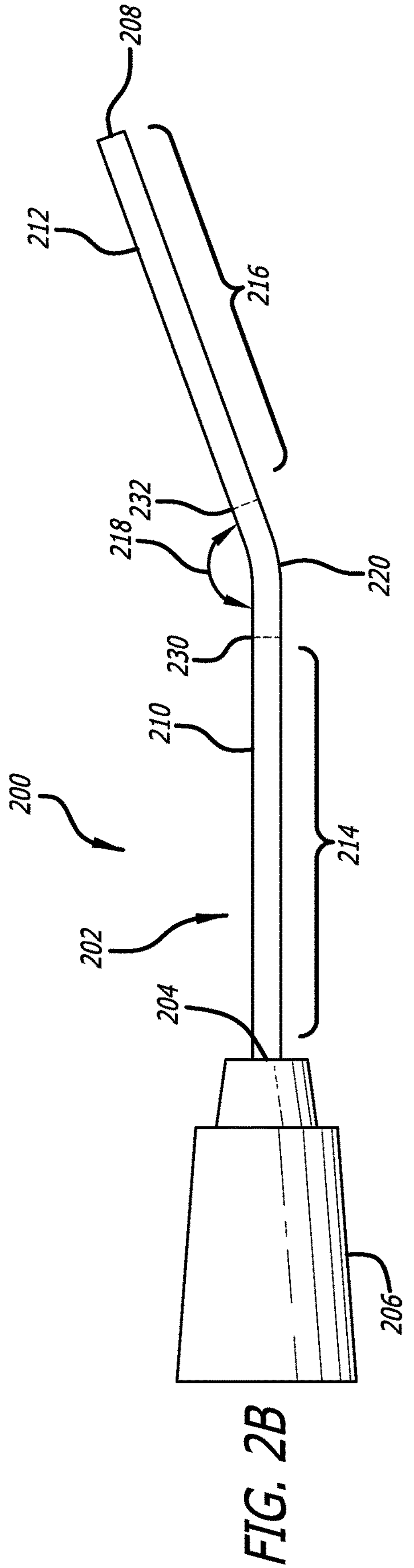

In some embodiments, as illustrated in FIG. 2B, the first transitional body segment 220 of the pre-curved catheter 200 can include an upward sloping first transitional body segment 220. For example, the angular displacement between the first end 230 and the second end 232 of the transitional body segment may be measured (and represented) by a first degree of curvature 218 (e.g., a bottom angular surface of the first end 230 to a corresponding bottom angular surface of the second end 232), which provides the angular change between a direction in the orientation of the first body segment 210 and a direction in the orientation of the second body segment 212. In some embodiments, the first degree of curvature 218 can include a positive obtuse angle and in some embodiments can be within the range of approximately 125°-176° as measured from the first reference point.

Figure 3A:
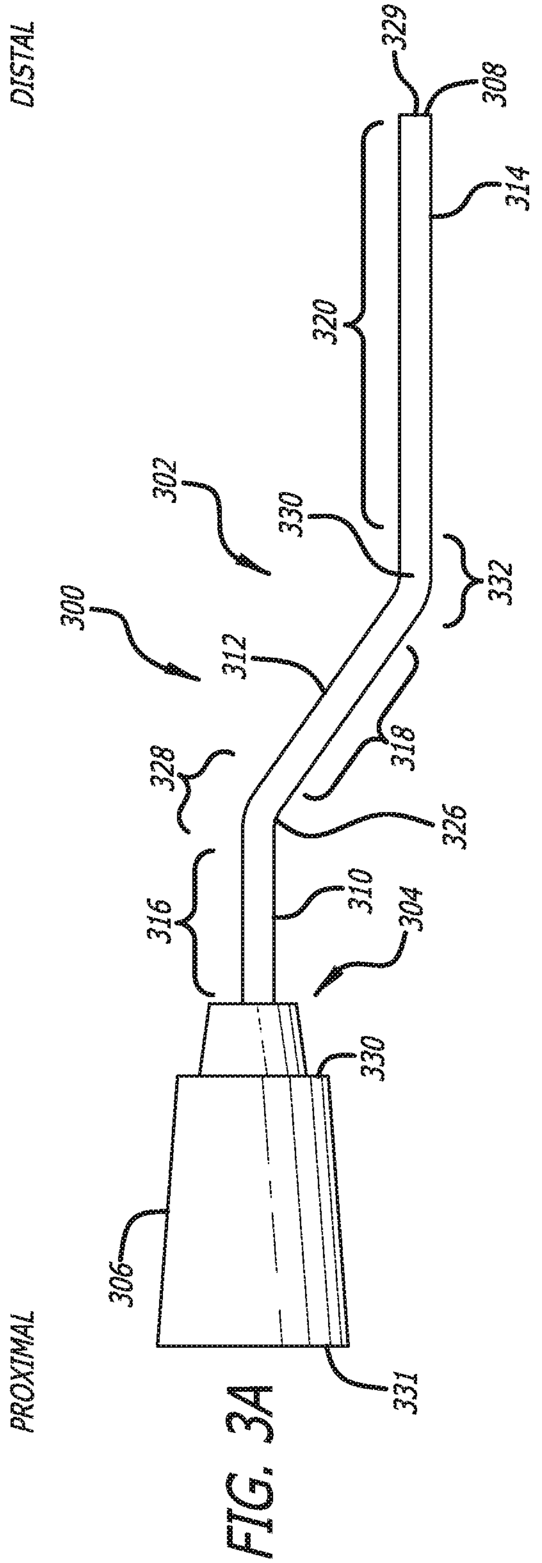
FIGS. 3A-3B illustrates a preferred embodiment of pre-curved catheter in accordance with some embodiments.

FIG. 3A illustrates different embodiments of a pre-curved catheter 300 in accordance with some embodiments. The pre-curved catheter 300 includes a molded hub 306, having a proximal end 328 and a distal end 330. The molded hub 306 is distally connected to an elastically deformable tubular body 302 having a proximal opening 304, distal opening 308 and a lumen 329 configured to receive and support an introducer needle having a diameter in the range of 14 gauge to 26 gauge.

In some embodiments, the elastically deformable tubular body 302 includes a first body segment 310, a second body segment 312, a third body segment 314, a first transitional body segment 326 and a second transitional body segment 330. The first body segment 310 having a first body segment length 316, the second body segment 312 having a second body segment length 318, and the third body segment 314 having a third body segment length 320. The first transitional body segment 326 features a first transitional body segment length 328 and the second transitional body segment 330 features a second transitional body segment length 332.

In some embodiments, the first body segment 310 is proximal the hub 306, the second body segment 312 is distal from the first body segment 310 with the first transitional body segment 326 interposed between the first body segment 310 and the second body segment 312. The third body segment 314 is distal the second body segment 312 with the second transitional body segment 330 interposed between the second body segment 312 and the third body segment 314. In some embodiments, the first transitional body segment 326 may include a downward sloping transitional body segment or an upward sloping transitional body segment.

Figure 3B:
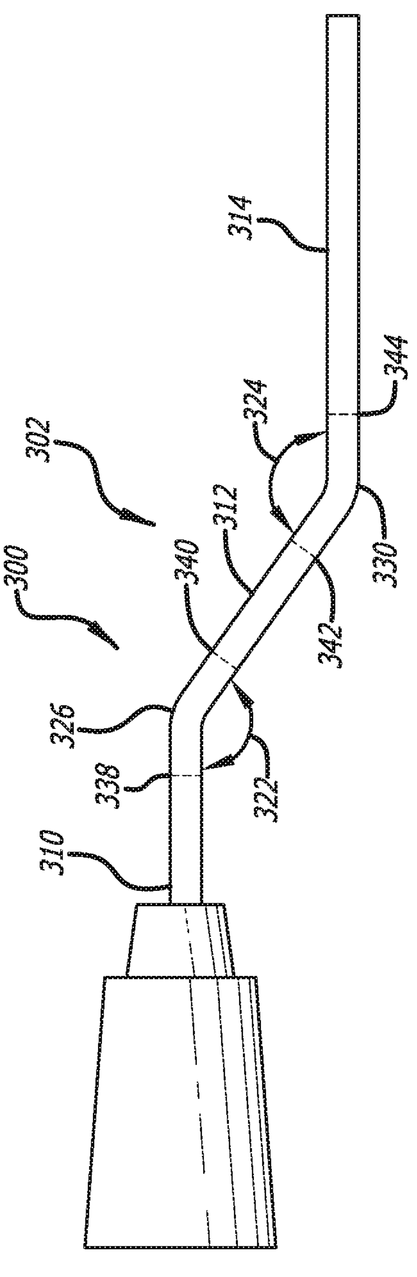

FIG. 3B illustrates the pre-curved catheter 300 including the downward sloping first transitional body segment 326 and the upward sloping second transitional body segment 330. The first transitional body segment 326 may be configured with a selected angular displacement between a first end 338 and a second end 340 of the first transitional body segment 326. For example, the angular displacement between the first end 338 and the second end 340 of the first transitional body segment 326 may be measured (and represented) by a first degree of curvature 322, which provides the angular change between a direction in the orientation of the first body segment 310 and a direction in the orientation of the second body segment 312. The first degree of curvature 322 can be measured from a first reference point that includes the first end 338 of the first transitional body segment 326.

In some embodiments, as shown in FIG. 3A, the second transitional body segment 330 can include a upward sloping transitional body segment or a downward sloping transitional body segment. The second transitional body segment 330 may be configured with a selected angular displacement between a first end 342 and a second end 344 of the second transitional body segment 330. The angular displacement between the first end 342 and the second end 344 of the second transitional body segment 330 may be measured (and represented) by a second degree of curvature 324 which provides the angular change between a direction in the orientation of the second body segment 312 and a direction in the orientation of the third body segment 314. The second degree of curvature 324 can be measured from a second reference point that includes first end 342 of the second transitional body segment 330.

In some embodiments, as illustrated in FIG. 3B, the first degree of curvature 322 can include a negative obtuse angle measured from the first reference point (e.g., a bottom angular surface of the first end 338 to a corresponding bottom angular surface of the second end 340 of the first transitional body segment 326). In some embodiments, the negative obtuse angle can be within a range from approximately −125° to −176° as measured from the first reference point. The second degree of curvature 324 can include a positive obtuse angle within the range from approximately 125° to 176° as measured from the second reference point (e.g., a top angular surface of the first end 342 to a corresponding top angular surface of the second end 344 of the second transitional body segment 330).

In other embodiments, the first degree of curvature 322 can include a positive obtuse angle as measured from the first reference point (e.g., a top angular surface of the first end 338 to a corresponding top angular surface of the second end 340 of the first transitional body segment 326) and the second degree of curvature 324 can include a negative obtuse angle as measured from the second reference point (e.g., a bottom angular surface of the first end 342 to a corresponding bottom angular surface of the second end 344 of the second transitional body segment 330). The positive obtuse angle of the first degree of curvature 322 can be within the range of approximately 125°-176° as measured from first reference point and the negative obtuse angle of the second degree of curvature 324 can be within the range of approximately −125° to −176° as measured from the second reference point. In accordance with a particular embodiment, the first degree of curvature 322 can include a negative obtuse angle, preferably −150° as measured from first reference point and the second degree of curvature 324 can include a positive obtuse angle, preferably 150° as measured from the second reference point. Advantageously, this particular embodiment has been demonstrated to reduce kink radius by approximately 10-15%.

Figures 4A, 4B, 4C, 4D:
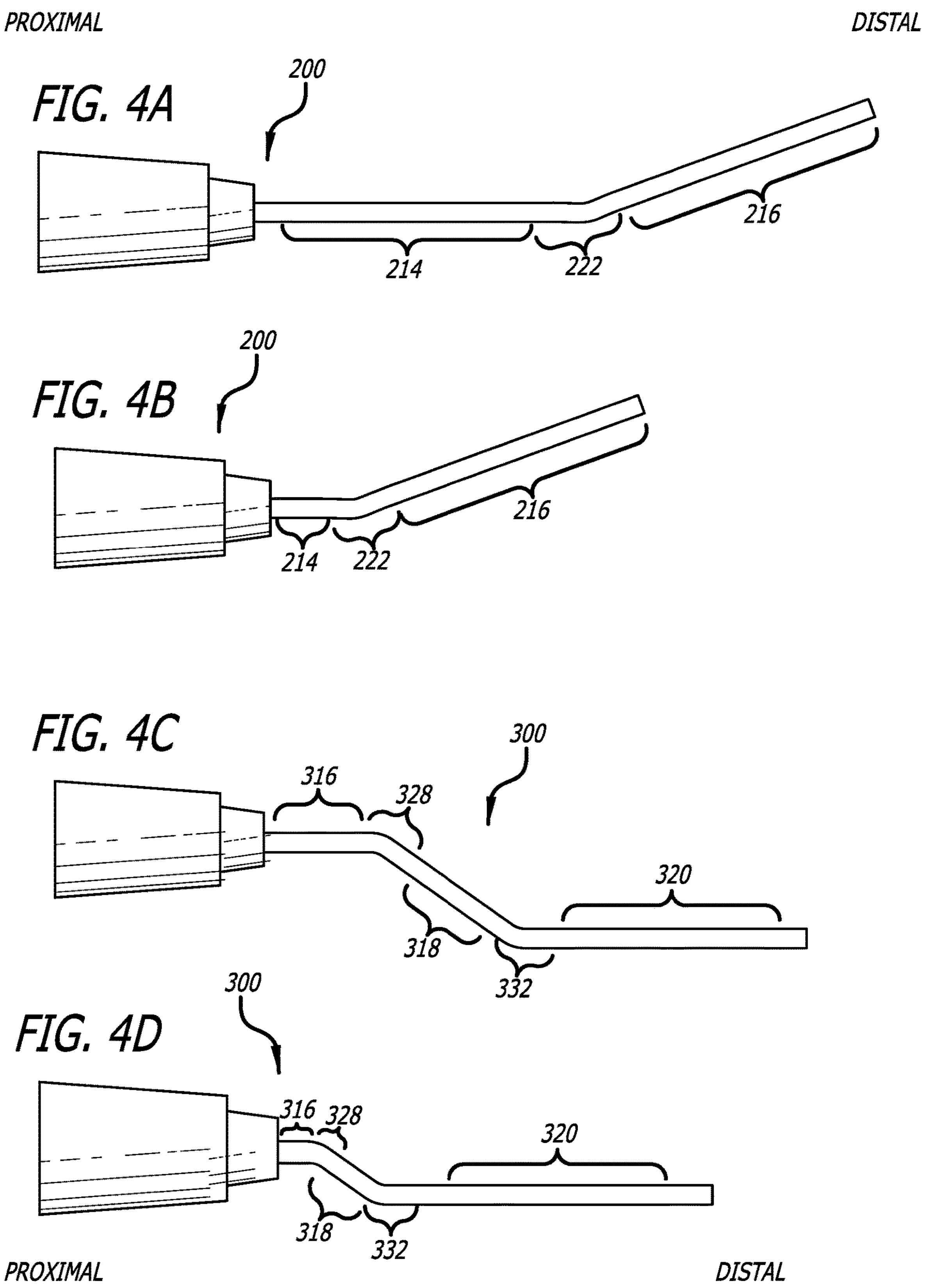
FIGS. 4A-4B illustrates a pre-curved catheter in accordance with some embodiments.
FIGS. 4C-4D illustrates a pre-curved catheter in accordance with some embodiments.

In some embodiments as illustrated in FIG. 4A, the pre-curved catheter 200 may include the first body segment length 214 and the second body segment length 216 being of the same length or being of varied lengths as illustrated in FIGS. 2A-2B. For example, the first body segment 214 may be less than or equal to the first transitional body segment length 222, which may be less than or equal to the second body segment length 216. For example, in FIG. 4B, the first body segment length 214 is less than the first transitional body segment length 222 which is less than the second body segment length 216. In some embodiments, the first body segment length 214 has a range of 0.01-0.13 inches, the second body segment length 216 has a range of 0.37-1.5 inches and the first transitional body segment length 222 has a range of 0.1-0.8 inches.

In some embodiments of the pre-curved catheter 300, the first body segment length 316, the second body segment length 318, the first transitional body segment length 328, the third body segment length 320 and the second transitional body segment length 332 may be of similar lengths. Alternative, the first body segment length 316, the second body segment length 318, the first transitional body segment length 328, the third body segment length 320 and the second transitional body segment length 332 may be of varied lengths as illustrated in FIG. 4C. For example, as illustrated in FIG. 4D, the first body segment length 316 may be less than or equal to the first transitional body segment length 328 which may be less than, greater than or equal to the second transitional body segment 332. The first transitional body segment length 328 may be less than, greater than or equal to the second transitional body segment length 332. The first transitional body segment length 328 and the second transitional body segment length 332 may be less than or equal to the second body segment length 318 which may be less than or equal to the third segment length 320.

In some embodiments, the first body segment length 316 can include a range of 0.001-0.130 inches, the second body segment length 318 can include a range of 0.37-1.5 inches and the third body segment length 320 can include a range of 0.53-2.375 inches. In some embodiments, the first transitional body segment length 328 can include a range of 0.10-1.6 inches and the second transitional body segment length 332 can include a range of 0.10-1.6 inches.

Figures 5A, 5B, 5C:
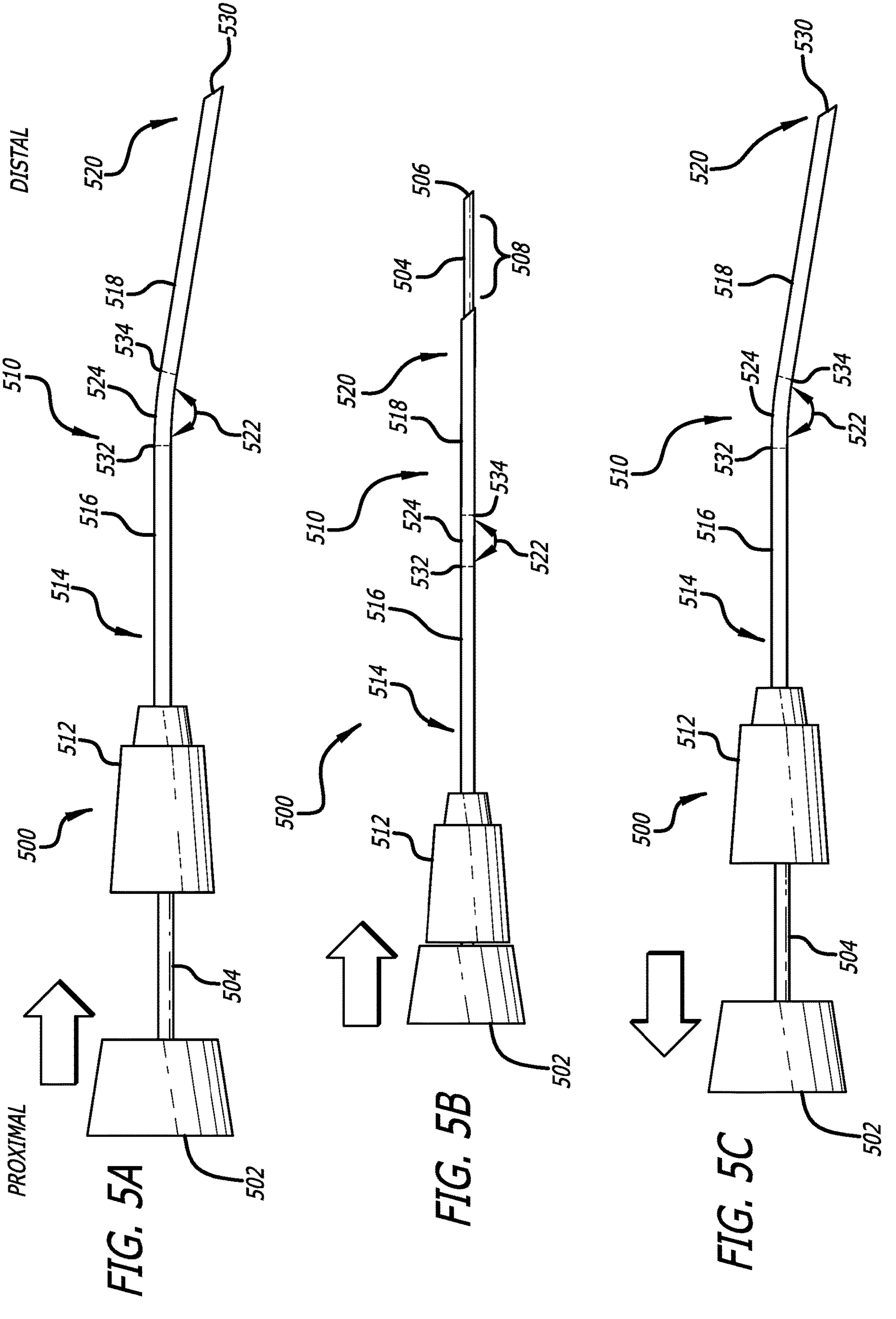
FIGS. 5A-5E illustrates a method of use of a pre-curved catheter in accordance with some embodiments.

FIG. 5A illustrated a catheter insertion kit 500 and method of use including a pre-curved catheter 510 and an introducer needle 502. The introducer needle 502 includes a rigid body 504 ending distally in a point 506 and having a diameter in the range of 14 gauge to 26 gauge. In some embodiments, the pre-curved catheter 510 includes a hub 512 distally connected to an elastically deformable tubular body 514 including a lumen 530 configured to receive and support the introducer needle 502 having a diameter in the range of 14 gauge and 26 gauge. The elastically deformable tubular body 514 includes a first body segment 516 proximal the hub 512, a second body segment 518 distal the first body segment 516, a first transitional body segment 524 interposed between the first body segment 516 and the second body segment 518.

The first transitional body segment 524 may be configured with a selected angular displacement between a first end 532 and a second end 534 of the first transitional body segment 524. The selected angular displacement can be measured and represented by a first degree of curvature 522, which provides the angular change between a direction in the orientation of the first body segment 516 and a direction in the orientation of the second body segment 518. The first degree of curvature can be measured from a first reference point including first end 532 of the first transitional body segment 524. In some embodiments, the catheter insertion kit 500 includes the pre-curved catheter 510 having first curved state wherein the first degree of curvature 522 includes a negative obtuse angle that may be in the range of −125° to −176° as measured from the first reference point. In some embodiments, the catheter insertion kit 500 includes the pre-curved catheter 510 having a second curved state wherein the first degree of curvature 522 includes a positive obtuse angle that may be in the range of 125° to 176° as measured from the first reference point.

In a method of use of the catheter insertion kit 500, the introducer needle 502 is inserted into lumen 530 of the elastically deformable tubular body 514. As illustrated in FIG. 5B, as the rigid body 504 moves completely distally through the lumen 530, the rigid body 504 applies a first external force on the first transitional body segment 524. The rigid body 504 changes the first degree of curvature 522 from a first curved state to a substantially horizontal state (e.g., when the first degree of curvature 522 is in the range of −179° to −181° or 179° to 181° as measured from the first reference point). As illustrated in FIG. 5C, the removal of the rigid body 504 on the first transitional body segment 524 returns the pre-curved catheter 510 to the first curved state. In some embodiments, the removal of the rigid body 504 on the first transitional body segment 524 returns the pre-curved catheter 510 to the second curved state.

Figure 5D:
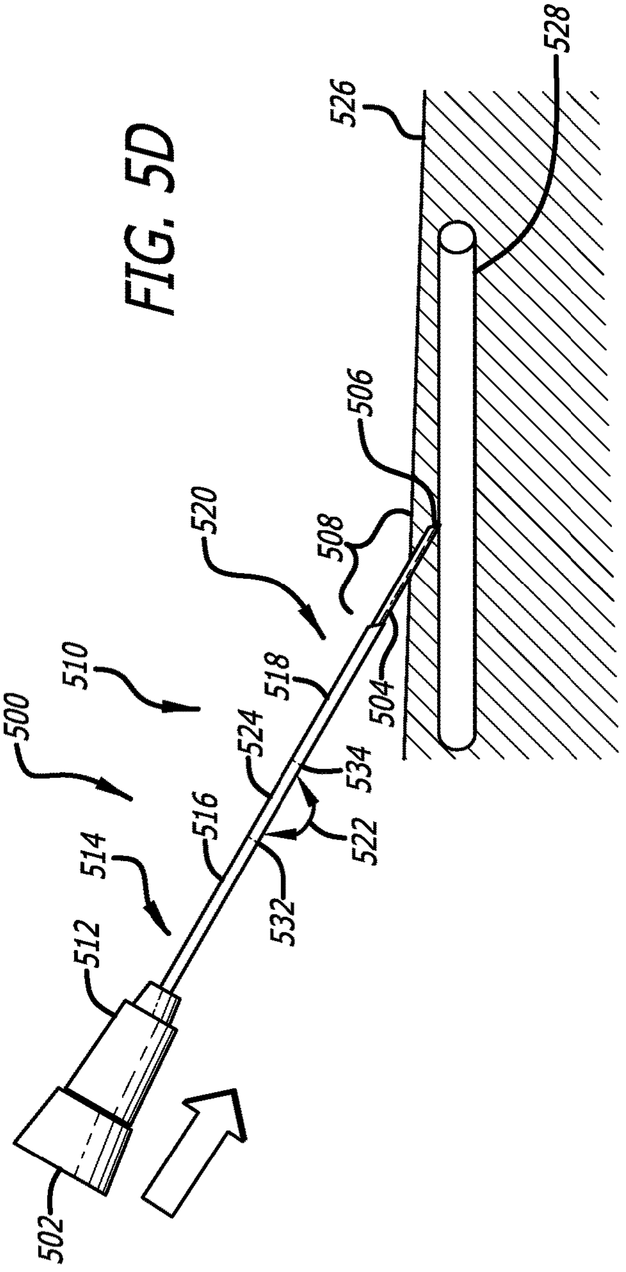

In some examples, as illustrated in FIG. 5D, the complete insertion of the rigid body 504 into the elastically deformable tubular body 514 includes a portion 508 of the rigid body 504 including the point 506 that extends past the distal end 520. When the pre-curved catheter 510 is the substantially horizontal state, the catheter insertion kit 500 is configured for the insertion of the pre-curved catheter 510 and the introducer needle 502 through the surface of the skin 526 into the lumen of the vessel 528.

Figure 5E:
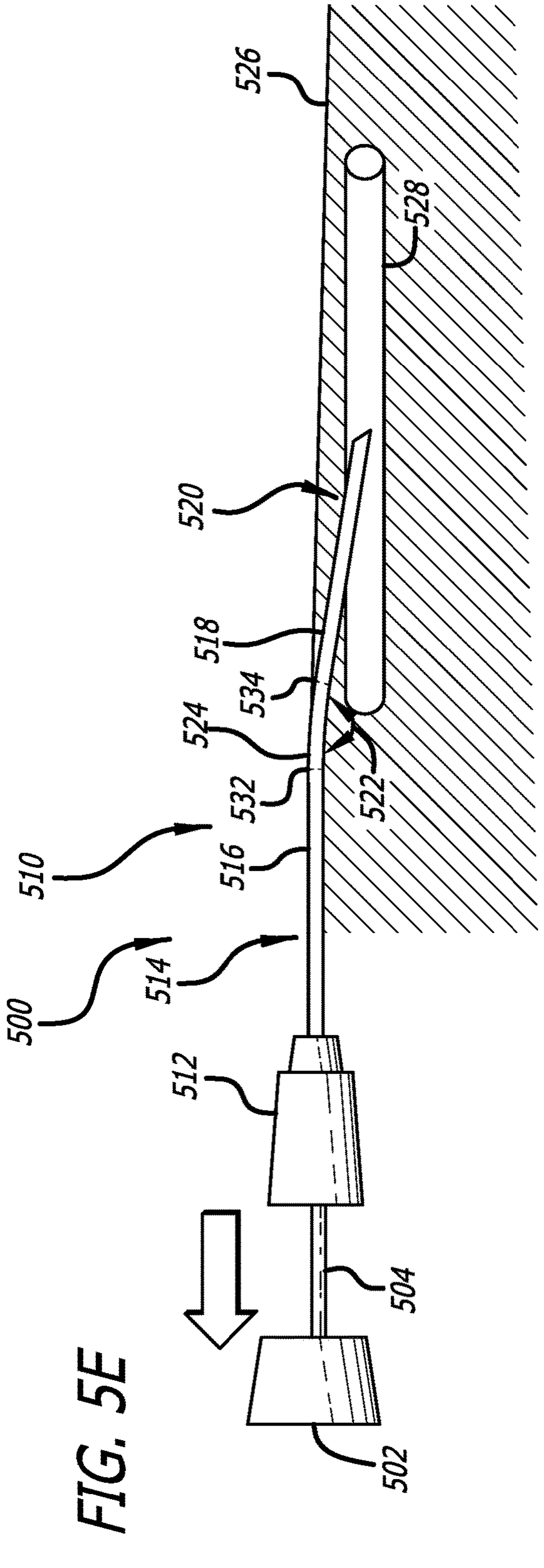

In some embodiments, as illustrated in FIG. 5E, once the distal end 520 of the pre-curved catheter 512 resides in the lumen of the vessel 528, the rigid body 504 is removed from the lumen 530. The removal of the rigid body 504 from lumen 530 removes the first external force on the first transitional body segment 524, allowing the pre-curved catheter 510 to return to the first curved state (e.g. when the first degree of curvature 522 includes a negative obtuse angle that may be in the range of −125° to −176° as measured from the first reference point being a bottom angular surface at the first end 532 of the first transitional body segment 524). In some embodiments, the pre-curved catheter 510 having the first curved state facilitates the second body segment 518 to remain in the lumen of the blood vessel 528 while the hub 512 of the pre-curved catheter can sit on the surface of the skin 526, reducing kink rates and extending the lifespan of the catheter.

Figures 6A, 6B, 6C:
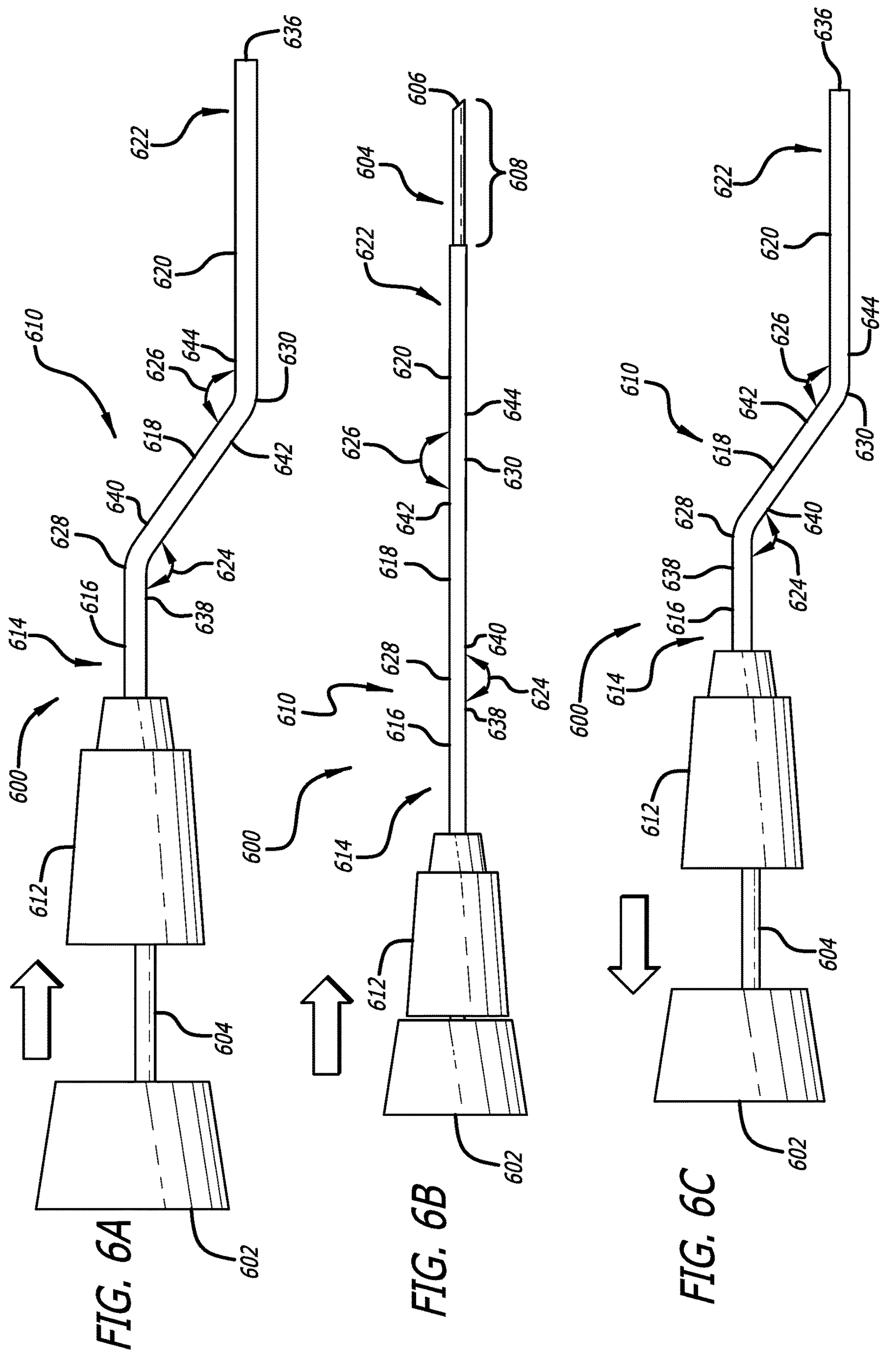
FIGS. 6A-6E illustrates a method of use of a pre-curved catheter in accordance with some embodiments.

FIG. 6A illustrated a catheter insertion kit 600 and method of use including a pre-curved catheter 610 and an introducer needle 602. In some embodiments, the insertion needle 602 includes a rigid body 604 ending distally in a point 606 having a diameter in the range of 14 gauge to 26 gauge. In some embodiments, the pre-curved catheter 610 includes a hub 612 distally connected to an elastically deformable tubular body 614 including a lumen 636 configured to receive and support an introducer needle 602 having a diameter in the range of 14 gauge to 26 gauge. The elastically deformable tubular body 614 includes a first body segment 616 proximal the hub 612, a second body segment 618 proximal the first body segment 616, a first transitional body segment 628 interposed between the first body segment 616 and the second body segment 618, a third body segment 620 distal the second body segment 618, and a second transitional body segment 630 interposed between the second body segment 618 and the third body segment 620.

The first transitional body segment 628 may be configured with a selected angular displacement between a first end 638 and a second end 640 of the first transitional body segment 628 and can be measured and represented by a first degree of curvature 624, which provides the angular change between a direction in the orientation of the first body segment 616 and a direction in the orientation of the second body segment 618. The first degree of curvature 624 can be measured from a first reference point including the first end 638 of the first transitional body segment 628. In some embodiments as illustrated in FIG. 6A, the catheter insertion kit 600 includes a pre-curved catheter 610 having a first degree of curvature including a negative obtuse angle in the range of −125° to −176° as measured from the first reference point.

The second transitional body segment 630 may be configured with a selected angular displacement between a first end 642 and a second end 644 of the second transitional body segment 630 and can be measured and represented by a second degree of curvature 626, which provides the angular change between a direction in the orientation of the second body segment 618 and the third body segment 620. The second degree of curvature 626 can be measured from a second reference point including the first end 642 of the second transitional body segment 630. In some embodiments as illustrated in FIG. 6A, the catheter insertion kit 600 includes a pre-curved catheter 610 having a second degree of curvature including a positive obtuse angle in the range of 125° to 176° as measured from the second reference point (e.g., as measured from a top angular surface near the first end 642 of the second transitional body segment 630 to a top angular surface near the second end 644 of the second transitional body segment 630).

The pre-curved catheter 610 may include a first curved state wherein the first degree of curvature 624 may include a negative obtuse angle and the second degree of curvature 626 may include a positive obtuse angle, In some embodiments, the pre-curved catheter 610 may include a second curved state wherein the first degree of curvature 624 may include a positive obtuse angle and the second degree of curvature 626 maybe include a negative obtuse angle.

In a method of use of a catheter insertion kit, the introducer needle 602 is inserted into lumen 636 of the elastically deformable tubular body 614. As illustrated in FIG. 6B, as the rigid body 604 moves completely distally through the lumen 636, it applies a first external force on the first transitional body segment 628 and the second transitional body segment 630. The rigid body 604 changes the pre-curved catheter 610 from a first curved state to a substantially horizontal state (e.g. when the first degree of curvature 624 is in the range of −179° to −181° as measured from the first reference point and the second degree of curvature 626 is in the range of 179°-to 181° as measured from the second reference point). In some embodiments, the rigid body 604 changes the pre-curved catheter 610 from a second curved state to a substantially horizontal state (e.g. where the first degree of curvature 624 is in the range of 179° to 181° as measured from the first reference point and the second degree of curvature 626 is in the range of −179° to −181° as measured from the second reference point).

As illustrated in FIG. 6C, the removal of the first external force on the first transitional body segment 628 and the second transitional body segment 630 by removal of the rigid body 604 allows the pre-curved catheter 610 to change from a substantially horizontal state back to a first curved state. In some embodiments, the removal of the first external force on the first transitional body segment 628 and the second transitional body segment 630 by removal of the rigid body 604 allows the pre-curved catheter 610 to change from a substantially horizontal state back to a second curved state.

Figure 6D:
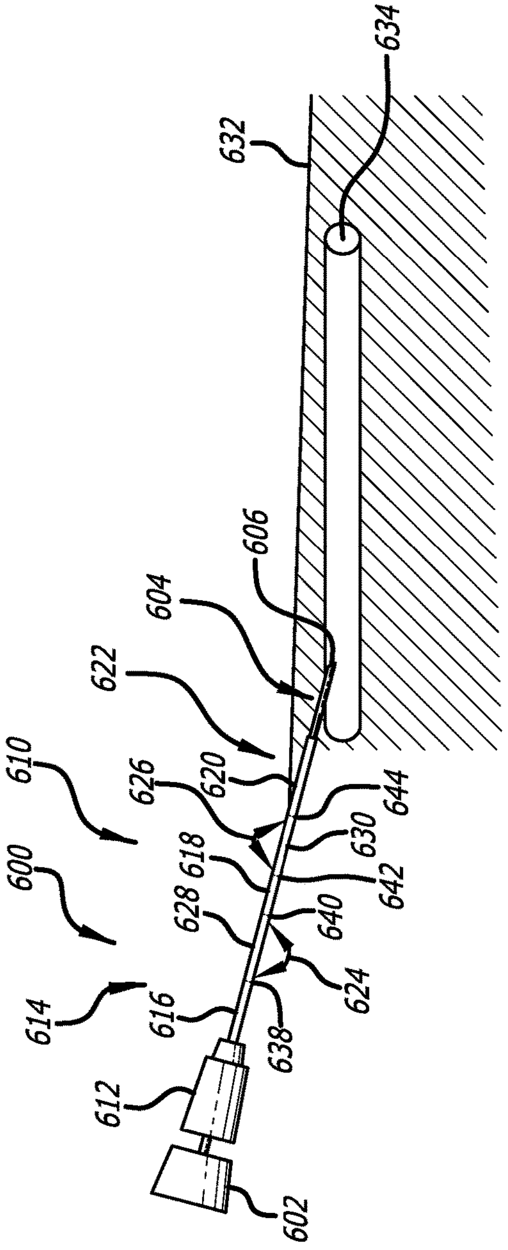

As illustrated in FIG. 6D, the complete insertion of the rigid body 604 of the insertion needle 602 into the lumen 636 includes a portion 608 of the rigid body 604 including the point 606 that extends past the distal end 622. When the pre-curved catheter is in the substantially horizontal state, the catheter insertion kit 600 is configured for insertion through the surface of the skin 632 into the lumen of the vessel 634.

Figure 6E:
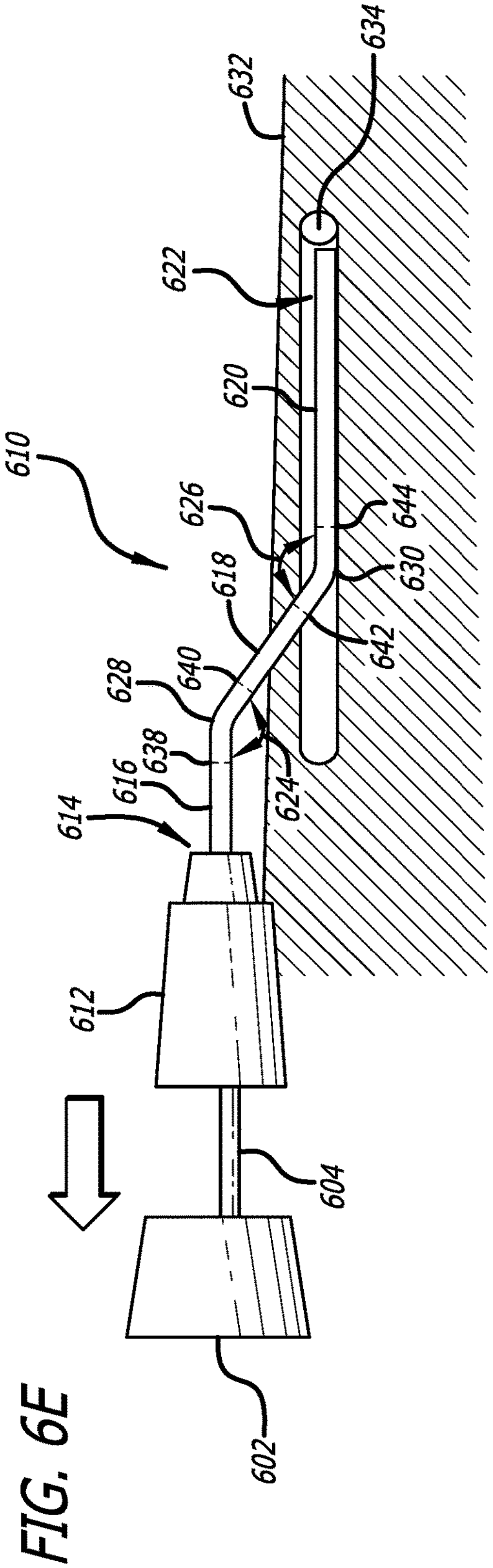

As illustrated in FIG. 6E, once the distal end 622 of the pre-curved catheter 610 resides in the lumen of the vessel 634, the rigid body 604 is removed from the lumen 636. The removal of the rigid body 604 from the lumen removes the first external force on the first transitional body segment 628 and the second transitional body segment 630, allowing the pre-curved catheter 610 to return to the first curved state. In some embodiments, the first curved state facilitates the third body segment 620 to remain in the lumen of the blood vessel 634 while the hub 612 of the pre-curved catheter 610 can sit on the surface of the skin 632, reducing kink rates and extending the lifespan of the catheter. In some embodiments, the removal of the rigid body 604 from the lumen removes the first external force on the first transitional body segment 628 and the second transitional body segment 630, allowing the pre-curved catheter to return to the second curved state. In some embodiments, the second curved state facilitates the third body segment 620 to remain in the lumen of the blood vessel 634 while the hub 612 of the pre-curved catheter 610 can sit on the surface of the skin 632.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A pre-curved catheter comprising:

a hub; and an elastically deformable tubular body coupled to the hub, the elastically deformable tubular body, comprising:

- a lumen extending along a length of the elastically deformable tubular body;
- a first body segment extending away from the hub;
- a second body segment disposed distal the first body segment, the second body segment including a second body segment length;
- a first transitional body segment interposed between the first body segment and the second body segment;
- a third body segment having a third body segment length, the third body segment disposed distal the second body segment; and
- a second transitional body segment having a second transitional body segment length interposed between the second body segment and the third body segment, wherein:

- the first body segment defines a first direction extending away from the first transitional body segment,
- the second body segment defines a second direction extending away from the first transitional body segment,
- the first transitional body segment defines a first angle between the first direction and the second direction,
- the first angle is an obtuse angle,
- the first transitional body segment includes a first transitional body segment length,
- the first body segment includes a first body segment length extending from the hub to the first transitional body segment,
- the first body segment length is less than or equal to the first transitional body segment length,
- the third body segment defines a third direction extending away from the second transitional body segment,
- the second body segment defines a fourth direction extending away from the second transitional body segment,
- the second transitional body segment defines a second angle between the third direction and the fourth direction,
- the second angle is an obtuse angle, and
- the first angle and the second angle face opposite directions.

2. The pre-curved catheter according to claim 1, wherein the first angle is within a range of 125° to 176°.

3. The pre-curved catheter according to claim 1, wherein the second angle is within a range of 125° to 176°.

4. The pre-curved catheter according to claim 1, wherein the elastically deformable tubular body is sized to support an introducer needle having a diameter in a range of fourteen (14) to twenty-six (26) gauge.

5. A catheter insertion kit comprising:

a pre-curved catheter including:

a hub; and an elastically deformable tubular body coupled to the hub, the elastically deformable tubular body comprising:

a lumen extending along a length of the elastically deformable tubular body;

a first body segment extending away from the hub;

a second body segment disposed distal the first body segment, the second body segment including a second body segment length;

a first transitional body segment interposed between the first body segment and the second body segment;

a third body segment having a third body segment length, the third body segment disposed distal the second body segment; and a second transitional body segment having a second transitional body segment length interposed between the second body segment and the third body segment, wherein:

the first body segment defines a first direction extending away from the first transitional body segment, the second body segment defines a second direction extending away from the first transitional body segment, the first transitional body segment defines a first angle between the first direction and the second direction, the first angle is an obtuse angle, the first transitional body segment includes a first transitional body segment length, the first body segment includes a first body segment length extending from the hub to the first transitional body segment, the first body segment length is less than or equal to the first transitional body segment length, the third body segment defines a third direction extending away from the second transitional body segment, the second body segment defines a fourth direction extending away from the second transitional body segment, the second transitional body segment defines a second angle between the third direction and the fourth direction, the second angle is an obtuse angle, and the first angle and the second angle face opposite directions; and an introducer needle including a rigid body having a proximal end, a distal end ending in a point, and a diameter in a range of 14-26 gauge, wherein the lumen is sized to receive the introducer needle for insertion and advancement through the lumen so that at least a portion of the rigid body extends past a distal end of the second body segment.

6. The catheter insertion kit according to claim 5, wherein the first angle is within a range of 125° to 176°.

7. The catheter insertion kit according to claim 5, wherein the second angle is within a range of 125° to 176°.

* * * * *